United States Patent [19]

Stolle et al.

[11] Patent Number: 4,732,757

[45] Date of Patent: * Mar. 22, 1988

[54] PREVENTION AND TREATMENT OF RHEUMATOID ARTHRITIS

[75] Inventors: Ralph J. Stolle, Lebanon, Ohio; Lee R. Beck, Birmingham, Ala.

[73] Assignee: Stolle Research and Development Corporation, Cincinnati, Ohio

[*] Notice: The portion of the term of this patent subsequent to Aug. 18, 1998 has been disclaimed.

[21] Appl. No.: 558,909

[22] Filed: Dec. 9, 1983

Related U.S. Application Data

[63] Continuation of Ser. No. 875,140, Feb. 6, 1978.

[51] Int. Cl.$^4$ ............... A61K 39/116; A61K 39/085; A61K 39/112; A61K 37/04
[52] U.S. Cl. ........................................ 424/87; 424/92
[58] Field of Search ..................... 424/85–92

[56] References Cited

U.S. PATENT DOCUMENTS

| | | | |
|---|---|---|---|
| 1,636,445 | 7/1927 | Small | 424/87 |
| 2,011,225 | 8/1935 | Krueger | 424/92 |
| 2,166,963 | 7/1939 | Masucci | 424/92 |
| 2,385,443 | 9/1945 | Hoffmann | 424/92 |
| 3,127,318 | 3/1964 | Eversole et al. | 424/92 |
| 3,128,230 | 4/1964 | Heinbach | 424/92 |
| 3,139,382 | 6/1964 | Killinger | 424/92 |
| 3,376,198 | 4/1968 | Petersen et al. | 424/92 |
| 3,461,200 | 8/1969 | Mathies | 424/85 |
| 3,480,610 | 12/1969 | Fox | 424/92 |
| 3,487,148 | 12/1969 | Fox | 424/92 |
| 3,532,790 | 10/1970 | Greenberg et al. | 424/92 |
| 3,553,317 | 1/1971 | Michaelson et al. | 424/87 |
| 3,626,057 | 12/1971 | Sarwar | 424/87 |
| 3,646,193 | 2/1972 | Michaelson et al. | 424/85 |
| 3,911,108 | 10/1975 | Singh | 424/86 |
| 3,917,818 | 11/1975 | Botes | 424/87 |
| 3,962,422 | 6/1976 | Parks | 424/89 |
| 3,975,517 | 8/1976 | Wilson | 424/87 |
| 4,051,235 | 9/1977 | Plymate | 424/85 |
| 4,141,970 | 2/1979 | Chidlow et al. | 424/92 |
| 4,160,825 | 7/1979 | Sikes | 424/85 |
| 4,284,623 | 8/1981 | Beck | 424/85 |
| 4,324,782 | 4/1982 | Beck | 424/87 |
| 4,377,569 | 3/1983 | Plymate | 424/87 |
| 4,402,938 | 9/1983 | Collins et al. | 424/85 |

FOREIGN PATENT DOCUMENTS

| | | | |
|---|---|---|---|
| 214582 | 9/1956 | Australia | 424/92 |
| 587849 | 12/1959 | Canada . | |
| 0064103 | 10/1982 | European Pat. Off. | 424/87 |
| 307975 | 4/1914 | Fed. Rep. of Germany | 424/87 |
| 516403 | 12/1930 | Fed. Rep. of Germany | 424/87 |
| 1161659 | 1/1964 | Fed. Rep. of Germany | 424/85 |
| 32472 | 10/1962 | Finland . | |
| 608596 | 9/1948 | United Kingdom | 424/88 |
| 837695 | 4/1955 | United Kingdom | 424/87 |
| 988175 | 4/1965 | United Kingdom . | |
| 1211876 | 11/1970 | United Kingdom . | |
| 1505513 | 3/1978 | United Kingdom . | |
| 2013691 A | 8/1979 | United Kingdom . | |

OTHER PUBLICATIONS

McGhee et al., J. Dent. Res., Special Issue C vol. 55 (1976), 206–214, Effective Immunity to Dental Caries: Studies of Active and Passive Immunity to Streptococus Mutans in Malnourished Rats.

(List continued on next page.)

Primary Examiner—Shep K. Rose
Attorney, Agent, or Firm—Frost & Jacobs

[57] ABSTRACT

There is disclosed a novel method and product for the treatment and prevention of rheumatoid arthritis. The method involves passive immunization against a mixed spectrum of infectious bacteria which reside in the human gastrointestinal tract. The passive immunization is accomplished by oral injection of IgG immunoglobulin obtained from the milk of cows that have been immunized against a specific spectrum of bacterial types. A unique combination of bacterial species is formulated into a vaccine which is used to immunize dairy cattle. The IgG antibody obtained from the milk of the immunized cows constitutes the product of the invention.

OTHER PUBLICATIONS

Lascelles Dairy Science Abstracts, vol. 25, No. 9 (1963), A Review of the Literature on Some Aspects of Immune Milk, pp. 359–364.

Holm, U.S. patent application Ser. No. 628,987 of Nov. 15, 1945, Abstract Published O.G. Dec. 5, 1950, 1 page, Spec. pp. 1, 3, 4, 5 and 7.

Karel, A Dictionary of Antibiosis, Columbia U. Press, N.Y. (1951) pp. 203–208.

Vaughan, (Hollander, Ed.) Arthritis and Allied Conditions, Lea and Febiger, Pa. 7th Ed. (1966) pp. 574–586.

Bauer, W., Clark, W. S. and Dienes, L. (1961) The Practitioner 166:5.

Lewis–Fanning, E. (1950), Ann. Rheum. Dis., Suppl. 9.

Sabin, A. B. (1939), Science 89:228.

Sikes, D., Neher, G. M. and Doyle, L. P., (1955), Am. J. Vet. Res. 16.

Figure 1

Monthly Questionnaire and Scoring Guide
Date_____

Please answer the questions by filling in the blank spaces or checking the boxes.

Name_____   Sex_____   Age_____

Race_____ Marital Status: ◯ Married    Employment: ◯ Full-time
                                          ◯ Unmarried              ◯ Part-time
                                          ◯ Widowed How long have you had arthritis? _____ years Score     1. This morning, did your stiffness last:

0              longer than 30 minutes
                    or
1              less than 30 minutes 2. This question is about your joint pains in just this past week only:

| JOINTS | NO PAIN Score 0 | PAIN LASTING ONE DAY OR LESS Score 1 | PAIN LASTING CONSTANTLY FOR MORE THAN ONE DAY Score 2 |
|---|---|---|---|
| a. Shoulders | | | |
| b. Elbows | | | |
| c. Wrists | | | |
| d. Hands | | | |
| e. Hips | | | |
| f. Knees | | | |
| g. Ankles | | | |
| h. Feet | | | |

3. Please tell us the drugs you took yesterday: (Pills)

Score        a. Aspirin                      ◯ Yes     How many yesterday?_____
Pills          (any form, Ecotrin,          ◯ No
                Bufferin, Anacin, etc.)

b. Cortisone                    ◯ Yes     How many yesterday?_____
mgx4           (any form)                   ◯ No c. Indocin                      ◯ Yes     How many yesterday?_____
Pills x 2.5    (blue & white                ◯ No
                capsules).

d. Pain Pills                   ◯ Yes     How many yesterday?_____
grx2           (Darvon, Codein              ◯ No
                etc.)

e. Butazolidin                  ◯ Yes     How many yesterday?_____
Pills x 7                                   ◯ No

Figure 1a

4. In the last 3 months, have you had: (Other medication)

| | | |
|---|---|---|
| Score 1 | Gold | ○ Yes |
| Score 2 | | ○ No |
| Score 1 | Plaquenil | ○ Yes |
| Score 2 | | ○ No |
| Score 1 | Cortisone Shots | ○ Yes |
| | | ○ No |

5. In the past month, are you: (ADL)

Score

1     ○ Able to carry out all normal activities, (work, housework, shopping)

2     ○ Able to carry out all normal activities but with some limitations (limited housework, limited shopping, etc.)

3     ○ Able to carry out only some of your normal activities because of joint problem 4     ○ Are you able to carry out only <u>a few</u> of your normal activities 5     ○ Are you very dependent on others for your own care 6     ○ Unable to get out of chair or bed by yourself 6. Tell us how your arthritis is bothering you. (Monthly change)

Score 1     a. Joint Pain:    ○ worse than last month
2                                  ○ same as last month
3                                  ○ less than last month 1     b. Morning Stiffness:    ○ longer than last month
2                                            ○ same as last month
3                                            ○ shorter than last month 1     c. Joint Swellings:    ○ worse
2                                   ○ same
3                                   ○ less

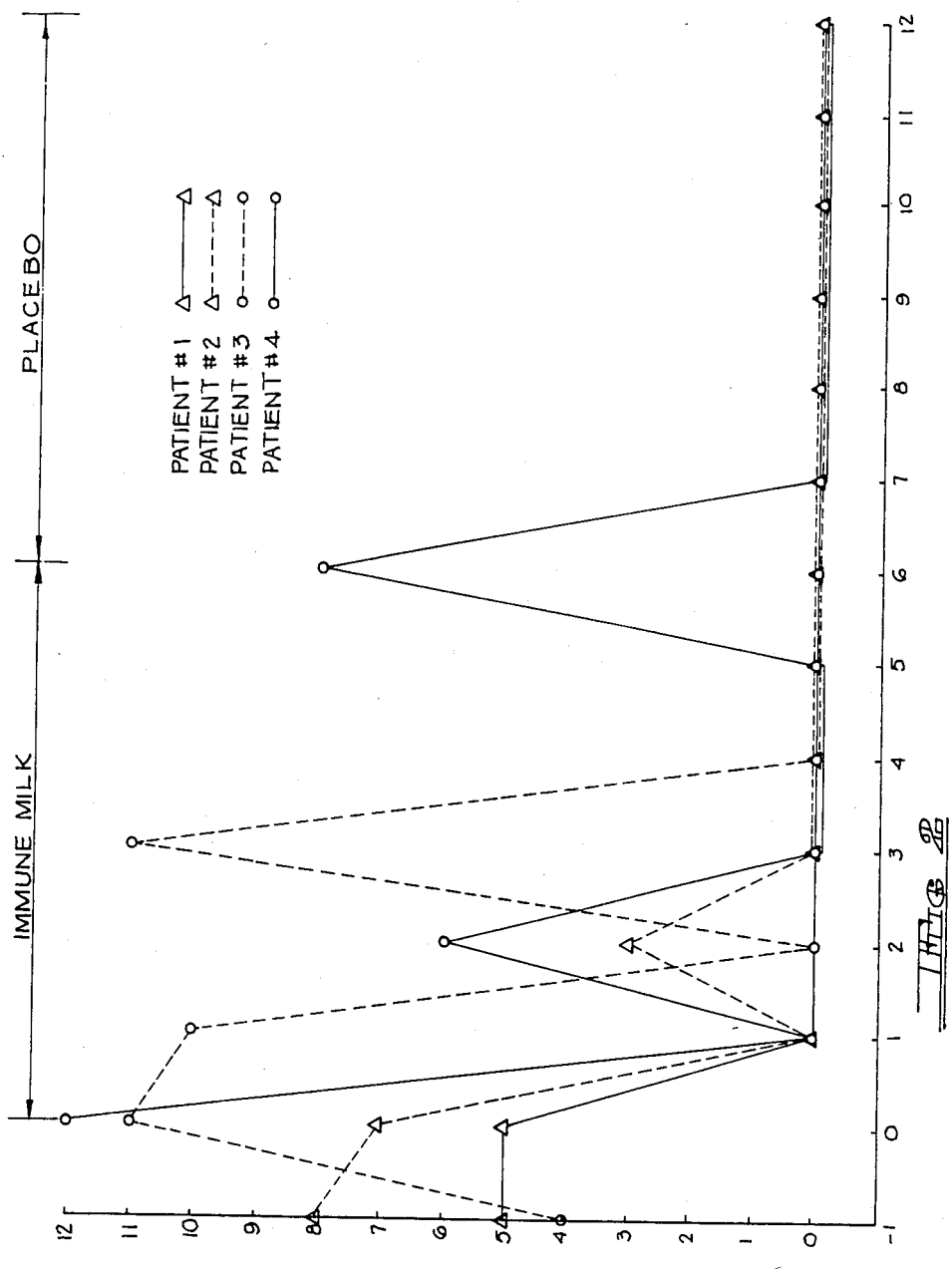

PREVENTION AND TREATMENT OF RHEUMATOID ARTHRITIS

This application is a continuation of application Ser. No. 875,140, filed Feb. 6, 1978.

REFERENCE TO RELATED APPLICATIONS

This application is related to an application in the name of Lee Randolph Beck, Ser. No. 776,249 filed March 10, 1977.

BACKGROUND OF THE INVENTION

A number of years ago it was commonly believed that rheumatoid arthritis had an infectious etiology. This view is not popular today, although the inflammatory features and constitutional manifestations of rheumatoid arthritis—the synovitis and granulomatous lesions, the fever, tachycardia, leukocytosis, lymphadenopathy and occasional spelnomegaly, the accelerated erythrocyte sedimentation rate and other changes in "acute phases reactants"—are all compatible with an infectious process. Competent and repeated bacteriologic studies have failed to recover consistently a single infectious agent from the blood, synovial fluid, synovial tissues or subcutaneous nodules. Attempts to transmit the disease by injecting joint fluid from patients with rheumatoid arthritis into the joints of other human subjects have been unsuccessful. Subcutaneous nodules have failed to survive following homologous transplantation (Bauer, et al, 1951) the Practitioner 166:5.

An infectious process may appear to precipitate the onset of rheumatoid arthritis in a significant number of patients, and may exert a deleterious influence on the course of the disease when it has already been established. There is statistical evidence to support this clinical impression (Lewis-Faning, 1950) Ann Rheum. Dis., Suppl. 9.

Many attempts have been made to produce a disease in animals similar to rheumatoid arthritis. While a variety of bacteria can produce arthritis in animals, they fail to reproduce the clinical and pathologic features of rheumatoid arthritis, particularly the self-perpetuating characters of the proliferative arthritis. Arthritis bearing some semblance to the human disease has been produced in mice by pleuro-pneumonia-like organisms (Sabin, 1939) Science 89:228, and in swine by Erysipelothrix rhusiopathiae (Sikes, et al, 1955). The concept that these organisms may initiate a hypersensitivity mechanism has been postulated (Sikes, et al, 1955).

Students of rheumatoid arthritis nevertheless continue to be intrigued by certain recurring themes that suggest relationships between infections and joint disease. Gonorrhea, for instance, is capable not only of producing typical gonorrheal arthritis but also of occasionally introducing chronic arthritis which evolved into typical rheumatoid arthritis. No statistics are available on the incidence with which this occurs, so one cannot know how much to stress the relationship. Tonsillitis or pharyngitis may also be followed by a polyarthritis, which at first appears to be rheumatic fever but which evolves into rheumatoid arthritis. Acute viral infections, especially rubella in young women, may be followed by persistent polyarthritides involving small joints as well as large; these arthritides generally run a several-month course of persisting joint disease resembling rheumatoid arthritis before gradually subsiding.

While chronic infection by an unknown agent remains a popular assumption for the etiology of rheumatoid arthritis, no published data exist to support the presumption. Some students of the disease suspect that if infection is a factor it may not be infection by any specific type of microorganism with an altered host response generated by the infections responsible for the disease. The present invention is based on this theory for the origin of rheumatoid arthritis.

Although an infectious etiology has never been established, several recent developments appear relevant in support of this theory.

Some of these are as follows:

1. Patients with rheumatoid arthritis have lower than normal levels of IgA, the class of immunoglobulin found in secretions of the gastrointestinal tract.

2. Immunoglobulin A produced in response to immunization via the salivary glands is found in serum colostrum and milk as well as in the saliva. It is suggested that the IgA is transported to these various fluids via the gastrointestinal tract and the lymphatic system (Michelok, et al, 1975) Proc. Soc. Exptl. Biol. Med. 148:1114.

3. Following an intestinal bypass operation for morbid obesity, certain patients develop symptoms that are virtually identical with rheumatoid arthritis. The onset of arthritis is accompanied by the appearance in blood serum of circulating cryoproteins composed of IgG, IgM, IgA, complement components $C_3$, $C_4$, $C_5$, and IgG antibody against *E. coli* and *B. fragilis*. Removal of the intestinal bypass results in complete remission of the symptoms (Woods, et al, 1976) New Engl. J. Med. 294:121.

4. A type of *Diplostreptococcus agalactiae* belonging to the streptococci group B has been implicated as an etiologic agent in rheumatoid arthritis (Svartz, 1972) Acta. Med. Scand. 192:231. This streptococcus is present in most commercially available pasteurized milk but not in immune milk.

5. A predisposition to rheumatic disease appears to be inherited via the histocompatibility antigens (HL-A). These antigens probably determine host response to infective agents.

On the basis of this evidence, it is concluded that rheumatoid arthritis has an infectious origin; the site of infection occurs in the gut; a number of different bacterial strains are involved in the infection; the infection probably results because of a failure in the host's immune defense mechanism; and the most effective way to treat the disease is to re-establish the immune protection against the infectious agent in the gut.

Treatment of Infection

There are basically two methods which may be used for the treatment of infection: the immune approach which involves either active or passive immunization against the infectious pathogens, and the use of antibiotics such as penicillin, tetracycline, ampicillin and the like. Antibiotics are not specific in their activity, and they kill a wide spectrum of beneficial as well as harmful bacteria. On the other hand, the immune approach is highly specific. Bactericidal antibodies produced against a specific strain of bacteria react only with that strain and have no harmful effects on other types of bacteria. Moreover, antibodies, unlike antibiotics, are natural body products and have no known side effects. Since the objective of the invention is to control infection by a specific group of bacteria, without harming beneficial bacteria in the gut, the immune approach is the method of choice.

Active and Passive Immunization

There are two different methods to achieve immune protection. Active immunization is a process whereby the host is actively immunized with a vaccine which stimulates the immune system of the host to produce protective antibodies against factors contained in the vaccine. Active immunization occurs under natural conditions when the host is exposed to infectious pathogens. Passive immunization is a process whereby antibodies obtained from one individual who has been actively immunized are given to a second individual. By this process, the protective antibodies are transferred from the immune host to the recipient. Passive immune protection is temporary and lasts only as long as the passively acquired antibodies persist in the system of the recipient. For example, antibodies collected from horses immunized against tetanus toxin can be given to humans infected with tetanus in order to obtain temporary immune protection against the toxin produced by tetanus bacteria. In a previous patent (U.S. Pat. No. 3,626,057) there is described a process for producing tetanus antitoxin in milk. This patent teaches that the cow can be actively immunized against tetanus toxin; that antibodies produced by the cow against the toxin can be obtained from the cow's milk; and that these antibodies can be used to treat animals infected with the tetanus bacteria in such a manner that the antibodies neutralize the toxin. The patent teaches that the passively administered antibodies neutralize the life-threatening toxin produced by the bacteria, thereby, providing temporary immunity against the toxin.

Passive immunization differs from active immunization in that the immune protection is temporary and lasts only as long as the protective antibodies are present. Active immunization is more permanent because the immune system of the host continues to produce protective antibodies in the presence of the stimulating antigen.

Recent studies in the field of gut immunology have shown the existence of a local immune mechanism in the gut. This immune system of the gut produces a special type of antibody which functions to control bacterial infestations in the lumen of the gut. The antibody called secretory immunoglobulin or IgA is produced in response to the local active immunization of the gut mucosa by the antigen. The secretory immune system of the gut functions to prevent the colonization and proliferation of harmful bacterial species in this environment. It is believed failure of the local immune system of the gut allows unknown harmful bacteria to become established and that this bacteria causes rheumatoid arthritis. According to this theory, rheumatoid arthritis results from a failure of the local immune system of the gut to produce and secrete protective antibodies against harmful bacteria. Thus, the inability of the host to respond to active immunization precludes this method as an approach to the treatment of rheumatoid arthritis.

The present invention describes a method for controlling the growth and proliferation of harmful bacterial pathogens—specifically, in the environment of the gastrointestinal tract of man; the method being that of passive immunization by oral ingestion of protective antibodies produced in the cow. The method provides temporary immune protection which is highly specific for those species of bacteria used to produce the antibodies and does no harm to the normal beneficial bacteria that reside in the gut. The antibodies used in the method of this invention constitute the unique and useful product of this invention.

Cow's milk provides the preferred source of the antibody product of the invention. It is very specific in that it defines a unique population of antibodies in milk (IgG type) that react with a known spectrum of bacteria and this reaction results in the beneficial effect, which is treatment and prevention of rheumatoid arthritis.

The type of immunoglobulin is an important consideration with regard to patentability of this invention because there are five known classes if immunoglobulin which are designated IgG, IgM, IgA, IgD, and IgE (Nisonoff, et al, 1971) Molecules of Immunity In Immunobiology. Eds., Good, R. A. and Fisher, W. Sinauer Ass., Stanford, Conn. (1971). Each type of immunoglobulin differs structurally (Waldman, et al, 1970) Plasma Protein Metabolism, Academic Press, p. 269 (1970), and has a different biological function within the body Waldman et al., Immune Mechanisms on Secretory Surfaces, Postgrad. Med. 50:78 (1971); and Franklin, Prog. Allerg., 8 p. 57 (1964). Moreover, there are striking variations in the locations of immunoglobulins within the body. For example, distribution clearly distinguishes immunoglobulin classes IgA and IgG. The most striking feature of IgA is its high concentration in external secretions of the body including the gastrointestinal fluid. It has been clearly shown that the immune system which contributes IgA to gastrointestinal fluid. It has been clearly shown that the immune system which contributes IgA to gastrointestinal fluid is a separate and distinct system from that which produces IgG.

In the human, IgG occurs primarily in the vascular and intracellular spaces of the body (Waldman, et al, 1970) Plasma Protein Metabolism, Academic Press, p. 269 (1970), and very little IgG finds its way into the gastrointestinal fluids. Another important difference between the classes of immunoglobulin is related to their metabolic rate. The degradation of each class of immunoglobulin, regardless of its location within the body, appears to be under separate control. The functional catabolic rate varies from as low as 6.5% for IgG to as high as 90% for IgE with other classes of immunoglobulin falling in between (Waldman, et al, 1970) Plasma Protein Metabolism, Academic Press, p. 269 (1970). Further, the different immunoglobulin classes also differ in their avidity with which the bind to antigens, and in their ability to combine with complement, which is one of the requisites for killing living bacterial cells (Heremans, 1960) Lesglobulenes Seriques du Systeme Gamma Leur Nature Et Leur Pathologie, Arscia Brusseles and Masson, Paris (1960). It is important to emphasize these differences in the types of antibodies because immune effects may vary depending on the type of antibody involved.

The most commonly held theory is that the different classes of immunoglobulin have evolved to function in different environments within the body. It is know, for example, that a special and distinct immune system exists for the production of antibodies which function in the environment of the gut. Moreover, there is general agreement that the immune functions of the gut are controlled specifically by IgA antibodies and not IgG. Therefore, under natural conditions, IgA is the class of immunoglobulin which regulates immune control over bacterial infections which occur in the gastrointestinal cavity of man. Since IgG, IgM, IgD, and IgE are not normally found in the intestinal secretions, it is not logical to expect that any of these types of antibodies would be effective in treating infections in the environment of the gut.

The principal immunoglobulin in the milk of cows is IgG, not IgA (Sullivan, et al, 1969) T. B. Jour of Immunol, 2, p. 103 (196). Therefore, bovine milk is not an obvious source of antibody for treating bacterial infections of the gut in man because of its high concentrations of IgG and low concentrations of IgA.

The method of immunization is another important parameter when considering the different classes of immunoglobulin. It is well-known to those skilled in the art that different methods of immunization result in the preferential production of different types of antibodies. For example, local immunization of secretory tissues achieved by exposing the tissue to antigens stimulates the preferential production and secretion of IgA type immunoglobulins. The technique of intramammory perfusion as described in the Petersen patent (U.S. Pat. No. 3,376,198) is an example of local immunization. This method stimulates production and secretion of IgA antibodies and is not an effective method for producing IgG.

According to the present invention, intramuscular injection is used to produce the product of the invention because IgG is the principal immunoglobulin in cow's milk, not IgA, and in the cow, systemic immunization is the preferred method for generating IgG type antibodies in milk. This distinction between the IgG and IgA type immunoglobulin is important because it teaches that systemic immunization and not local immunization is the preferred method for obtaining milk antibodies of high titer. Moreover, this distinction teaches that the immune products produced by mammary perfusion of a vaccine are distinctly different from the immune product produced by intramuscular injection of the identical vaccine. Thus, the product of this invention (IgG antibodies) is distinctly different from the product obtained by the Petersen process.

The immune product of this invention is an improvement over the product of Petersen's invention because the concentration of antibodies of the IgG type is significantly higher than the concentration of antibodies of the IgA type. There is no evidence in the literature to support the claim that IgG antibodies can be produced by intramammary perfusion of antigens. Mover, since the levels of IgA immunoglobulins are either non-extant or extremely low in cow's milk, it is unreasonable to suggest that the teaching of Petersen's patent has any relevance to the claim of this invention. On the contrary, the teaching of the Petersen patent leads away from the discovery of this invention since it implies that IgA is a biologically active factor in cow's milk, which has potential therapeutic application.

BRIEF SUMMARY OF THE INVENTION

According to the present invention, a unique combination of bacterial species is formulated into a vaccine, which is administered to healthy dairy cows. The IgG antibodies obtained from the milk of the immunized cows constitute the products of the invention. The method of the invention involves the passive immunization of the patient by oral injection of the IgG immunoglobulin, which passively immunizes against a mixed spectrum of infectious bacteria which reside in the gastrointestinal tract. This treatment eliminates conditions in the gastrointestinal tract which cause rheumatoid arthritis.

BRIEF DESCRIPTION OF THE FIGURES OF THE DRAWINGS

FIG. 1 is a specimen of a questionnaire referred to in the specification.

FIG. 1a is a continuation of the questionnarire of FIG. 1.

FIG. 2 is a graph plotting results of test in terms of RF titer against time, over a 12 month period, 6 months on immune milk and 6 months on placebo.

DETAILED DESCRIPTION

The product of this invention is a low-fat powered milk which optimally contains a population of natural IgG type antibodies that react with the bacterial species listed in Table 1.

TABLE 1

| Bacterial Antigens | |
|---|---|
| ORGANISM | *ATCC NO. |
| Staphylococcus aureus | 11631 |
| Staphylococcus epidermidis | 155 |
| Streptococcus pyogenes, A. Type 1 | 8671 |
| Streptococcus pyogenes, A. Type 3 | 10389 |
| Streptococcus pyogenes, A. Type 5 | 12347 |
| Streptococcus pyogenes, A. Type 8 | 12349 |
| Streptococcus pyogenes, A. Type 12 | 11434 |
| Streptococcus pyogenes, A. Type 14 | 12972 |
| Streptococcus pyogenes, A. Type 18 | 12357 |
| Streptococcus pyogenes, A. Type 22 | 10403 |
| Aerobacter aerogenes | 884 |
| Escherichia coli | 26 |
| Salmonella enteritidis | 13076 |
| Pseudomonas aeruginosa | 7700 |
| Klebsiella pneumoniae | 9590 |
| Salmonella typhimurium | 13311 |
| Haemophilus influenzae | 9333 |
| Streptococcus viridans | 6249 |
| Proteus vulgaris | 13315 |
| Shigella dysenteriae | 11835 |
| Streptococcus, Group B | |
| Diplococcus pneumoniae | |
| Streptococcus mutans | |
| Corynebacterium, Acne, Types 1 & 2 | |

*American Type Culture Collection, 12301 Parklawn Dr., Rockville, Md. 20852

The antibacterial milk contains all of the substances normally found in low-fat powdered milk. The principal constituents comprising antibacterial milk are shown in Table 2.

TABLE 2

| Quantitative and Qualitative Analysis of Antibacterial Milk | |
|---|---|
| Proteins | 35.6% |
| Fat | 1.0% |
| Carbohydrates | 52% |
| Minerals | 7.8% |
| Moisture | 3.5% |
| Each reliquified quart of 3-4 ounces of non-fat dry milk contains approximately: | |
| 1200 mg calcium | 157% |
| 935 mg phosphorous | 125% |
| 0.3 mg thiamine | 32% |
| 1.78 mg riboflavin | 140% |
| 1.04 mg niacin | 10% |
| 324 Calories | |

Antibacterial milk and normal cow's milk contain the same approximate percent by weight concentration of ingredients. Moreover, the concentration of type IgG immunoglobulin in antibacterial milk and normal milk is identical. Therefore, it is only the specificity of antibodies comprising the antibacterial milk which distinguishes it from normal milk. By specificity of the immunoglobulin is meant the spectrum of bacterial species that the antibodies react with.

Antibacterial milk contains no drug additives or any other components which are not natural food products of the cow.

The immune milk of the present invention is also useful in the control of auto-immune diseases, e.g. lupus erythematosus and the like, which are caused or aggravated by bacterial infections in the gastrointestinal tract.

The polyvalent antigen used for the induction of antibacterial milk is prepared as follows:

Preparation of the Vaccine

The bacterial strains listed in Table 1 were obtained from the American Type Culture Collection, which ensures authenticity of bacterial strains and the highest standard of purity that is available. Upon receipt, each individual bacterial strain was grown on a blood agar plate to test the viability of the culture and to determine if growth pattern is typical or atypical of the bacteria in question. A single colony from each of the test cultures was taken for histological examination to further ensure authenticity and purity of the culture. A single colony of each culture was used to inoculate 500 ml of standard culture broth. The standard broths recommended by the American Type Culture Collection were used to grow each of the specific bacteria listed in Table 1.

All organisms were incubated as static cultures with the exception of 12, 13, 14 and 16, which were incubated in the shaker to provide agitation. Identification of bacterial strains and the American Type Culture Collection catalog numbers are shown in Table 1. Each culture was cultivated for 48 hours at 37° C. Following incubation, the cultures were killed by heating at 60° C. for two hours. Samples of the killed bacteria were used to inoculate fresh broth which was then incubated for 24 hours at 37° C. to determine if the filling process was complete. Only cultures proven sterile by this procedure were used for further processing. Sterile cultures were then washed five times in distilled water and the cells were recovered by centrifugation. The bacterial cells were frozen by immersion in liquid nitrogen and freeze-dried by the process of lyophilization. The lyophilized cells were stored in sterile vials until used for production of the polyvalent vaccine. The polyvalent vaccine was prepared by weighing out one gram quantities of each of the bacterial strains. The dry cells were mixed together and this mixture was suspended in sterile physiological saline (20 grams of bacteria per 500 ml saline).

A sample of the concentrated solution was diluted in serial fashion with saline to determine dilution which gives a concentration of $4 \times 10^8$ ml per cc. The stock concentrated polyvalent vaccine was diskpersed into multiple containers and stored frozen. A sufficient amount of concentrated antigen was included in each individual container to immunize 50 cows. The final dilution of concentrate was made just prior to immunization. The preferred procedure is to remove a sufficient number of vials to immunize the number of cows to be treated. For example, the vials are removed 24 hours prior to the planned time of immunization; a sample of the concentrate is then diluted in a sterile container to a final concentration of $4 \times 10^8$ cells per ml. The maximum response in cows is obtained by injecting $20 \times 10^8$ bacterial cells or 5 cc of the sterile preparation which is $4 \times 10^8$ cells per ml according to the method of immunization described below.

Preferred Process for Immunization of Cows

The antibody product of the invention is produced by immunizing cows with the polyvalent antigen prepared as described above. The cows are injected with 5 cc of polyvalent antigen containing $20 \times 10^8$ bacterial cells. The injection is made intramuscularly in the gluteus maximus muscle of the hind leg. This procedure is repeated at one week intervals for four consecutive weeks beginning 2-3 weeks prior to the predicted day of parturition. Following the primary immunization, booster injections using the same concentration of the antigen, are given every 14 days. This method of immunization gives the maximum antibody titer.

Collection, Handling and Processing of Milk

The milk is collected from immunized cows in a modern dairy parlor. A fully automated milking system collects and stores the milk under complete sanitary conditions. The milking system consists of automated machines connected directly to refrigerated storage tanks by a closed system of pipes. The complete system is cleaned and sterilized following each milking to ensure maximum sanitary conditions. It is important to take careful steps to prevent the growth of bacteria to immune milk during processing, since such bacteria can lower the titer of antibodies in the milk.

Milk is transported daily from the refrigerated holding tanks to a dairy processing plant by milk transport trucks. At the dairy plant a high temperature short-time system is used to pasteurize the antibacterial milk. Specialized dairy machinery provides the flash heating of a continuous flow of milk to 155° F. for a period of not more than 15 seconds. Temperature and time is critical since antibody is susceptible to degradation by heat. Milk antibody is destroyed at temperatures above 165° F., if held for periods longer than one minute. Following pasteurization, the whole milk is immediately cooled and the fat is removed by centrifugation, and the skimmed whole antibacterial milk is powdered by a spray process. The spray process consists of a large drying chamber into which hot air (350° F.) is blown at high velocity. The skimmed milk is atomized into the chamber where the finely divided milk particles are instantly dried as they fall to the bottom of the tank. The dried milk is removed automatically by means of mechanical devices and the milk powder is packaged under sanitary conditions. Prior to atomizing, the skimmed milk is condensed by boiling in a chamber under vacuum (100°-110° F.). At each step it is critical to keep the bacteria from contaminating the milk since this reduces the titer of the antibody.

Testing Procedures

Immune milk was prepared in inbred Holstein cows. The cows were immunized by the intramuscular injection of a mixture of bacterial antigens identified in Table 1. The vaccine was prepared by the process described above. The immunologic response of the cows was boosted by bi-weekly injections of the vaccine. The milk from these cows was pooled, the fat removed, and the non-fat milk was pasteurized by exposure to 162° F. for 16 seconds followed by a spray-drying process in which the temperature of the milk did not exceed 85° F. The milk was packaged in one quart polyethylene containers. Control milk (placebo) was non-fat powedered milk purchased from a local producer.

Erythrocyte sedimentation rates were determined on freshly collected blood by the method of Westergren and corrected for hematocrit according to the method of Wintrobe & Landsberg (1935). Rheumatoid factor titers were determined by the Singer-Plotz (1966) macroscopic tube test.

Patients were accepted for the study on the basis of an elevated erythrocyte sedimentation rate and a positive rheumatoid factor titer. Nine patients were studied for 12 months and 11 patients were studied 18 months. The patient group was composed of thirteen caucasian females ranging in age from 32 to 69 years with an average of 50.4 years, and seven caucasian males ranging in age from 43 to 70 years with an average age of 58.1 years. The mean duration of arthritis was 10.8 years for the females and 11.0 for the males. Patients were randomly placed either on immune milk or on non-immune milk (a commercial product purchased in the Dayton area that served as a placebo). Both milk products were packaged in identical containers and were identified as being immune milk or placebo, respectively, by a blue or red pressure-sensitive label that was attached to each container at the time it was filled. The labels were removed just prior to dispensing the milk to the patients. Thus, at no time did the patients know whether they were receiving immune milk or placebo. Patients were randomly (as determined by the flip of a coin) selected to receive either immune milk or the placebo during the first six-month period. At the end of this time, those that were receiving immune milk were placed on the placebo and those that were receiving placebo were placed on immune milk for the second six-month period.

At the end of the second six-month period, 11 patients volunteered to remain on the study for an additional six months. The type of milk (immune or placebo) was again changed at this time and observations were continued. Thus, the study was comprised of three six-month periods, 11 of the patients participating for three periods and nine participating for two periods. Patients were seen at monthly intervals at which time a one month supply of milk was dispensed, an evaluation questionnaire was filled out and a blood sample was collected for rheumatoid factor titer, erythrocyte sedimentation rate and hematocrit determination.

Patients were instructed to take a quantity of non-fat milk solids equivalent to one quart of milk post prandially two times daily. The milk solids were freshly dissolved in one pint of cool tap water immediately before ingestion shortly after awakening in the morning and again just prior to retiring at night. They were told to see their physician as usual and to follow the treatment regimens prescribed by him. Medication was to be taken ad libitum or as prescribed by their regular doctor. We requested only that they report the quantity of medicines taken.

A questionnaire was completed by each patient at monthly intervals. It was divided into six sections that deal with:

(1) duration of morning stiffness,
(2) severity of pain experienced in each of eight joints,
(3) type and quantity of drugs with short-term actions that were taken,
(4) type and quantity of drugs with long-lasting actions that were taken,
(5) ability of patient to conduct his normal activities, and
(6) severity of symptoms of rheumatoid arthritis.

The numbers shown in the spaces next to each answer indicate the score assigned to that answer in the course of evaluting the questionnaires. In scoring the sections dealing with medications, an effort was made to reflect the relative anti-inflammatory and analgesic activities of the various drugs used. A five-grain aspirin tablet as assigned a value of one. All other drugs (with the except of gold, plaquenil and cortisone shots which were considered separately) were arbitrarily assigned values relative to aspirin. Thus, all salicylate preparations, Tylenol, Darvon, Motrin, etc. were considered equivalent to a five-grain aspirin tablet and were also assigned a value of one. The number of mg of Prednisone was multiplied times four, the number of Indocin capsules taken was multiplied times 2.5. The number of grains of codeine was multiplied times two, and the number of Butazoladin tablets taken was multiplied times seven.

The mean scores in each category were calculated for each six-month period. The differences of the means were then calculated by subtracting the mean values scored during administration of immune milk from those scored during administration of placebo. When the results were calculated in this manner, improvement in the patient's condition during the period he received immune milk was indicated by negative values for questions one and six, and by positive values for all other questions. Mean corrected erythrocyte sedimentation rates (ESR) and rheumatoid factor titers (RF) were respectively shown in a similar manner. These were calculated in such a way that positive values reflect a lower erythrocyte sedimentation rate or rehumatoid factor titer during administration of immune milk. The data were statistically evaluated using the Statistical Analysis System of Goodnight et al. (Computer Program Used for the Statistical Analyses, Statistical Systems Institute, Raleigh, N.C.). Calculations were performed with the aid of an IBM model 370/155 computer.

Results

The immune milk was well tolerated by all patients with the exception of one who had pernicious anemia. This patient complained of diarrhea and was terminated from the study. Some patients reported a weight gain during the course of the study. This may have been due to the increased caloric intake from the milk or possibly reflects a generalized improvement in their physical condition.

TABLE 3

| | Periods of Observation | | Treatment Regimen | | | | | |
| | | | Placebo | | Immune | | Mean | |
| | Control | Immune | Mean | C.V.* | Mean | C.V.* | Difference | P |
|---|---|---|---|---|---|---|---|---|
| 1. A.M. Stiffness | 27 | 24 | 0.332 | 95.7 | 0.679 | 35.6 | −0.347 | 0.0001 |
| 2. Joint Pain | | | | | | | | |

TABLE 3-continued

|  |  | Periods of Observation | | Treatment Regimen | | | | Mean Difference | P |
| --- | --- | --- | --- | --- | --- | --- | --- | --- | --- |
|  |  | | | Placebo | | Immune | | | |
|  |  | Control | Immune | Mean | C.V.* | Mean | C.V.* | | |
|  | a. Shoulder | 27 | 24 | 0.954 | 67.1 | 0.716 | 60.2 | +0.238 | 0.0420 |
|  | b. Elbow | 27 | 24 | 0.752 | 83.7 | 0.613 | 65.9 | +0.139 | 0.0511 |
|  | c. Wrist | 27 | 24 | 0.824 | 73.6 | 0.539 | 74.8 | +0.285 | 0.0010 |
|  | d. Hand | 27 | 24 | 1.073 | 54.7 | 0.828 | 56.5 | +0.245 | 0.0011 |
|  | e. Hip | 27 | 24 | 0.533 | 90.3 | 0.227 | 135.0 | +0.306 | 0.0005 |
|  | f. Knee | 27 | 24 | 0.904 | 74.1 | 0.683 | 59.0 | +0.221 | 0.0015 |
|  | g. Ankle | 26 | 22 | 0.7811 | 66.9 | 0.659 | 65.7 | +0.1221 | 0.0127 |
|  | h. Feet | 26 | 22 | 0.948 | 63.7 | 0.729 | 50.9 | +0.219 | 0.0010 |
| 3. | Pills | 27 | 24 | 20.663 | 104.1 | 16.515 | 101.3 | +4.148 | 0.0405 |
| 4. | Other Medication | 27 | 24 | 0.325 | 140.7 | 0.244 | 175.6 | +0.081 | 0.0276 |
| 5. | ADL | 27 | 24 | 2.224 | 36.1 | 1.874 | 29.1 | +0.350 | 0.0023 |
| 6. | Monthly change | | | | | | | | |
|  | a. Pain | 27 | 24 | 1.903 | 21.8 | 2.247 | 14.1 | −0.344 | 0.0042 |
|  | b. Stiffness | 27 | 24 | 1.985 | 18.8 | 2.254 | 12.4 | −0.269 | 0.0024 |
|  | c. Swelling | 27 | 24 | 1.924 | 17.9 | 2.117 | 13.3 | −0.193 | 0.00153 |
| 7. | ESR | 25 | 23 | 36.293 | 29.7 | 35.922 | 38.2 | +0.371 | 0.7376 |
| 8. | RF | 27 | 24 | 6.698 | 45.5 | 6.834 | 41.7 | −0.136 | 0.9635 |

*Coefficient of variation.

As shown in Table 3, patients were observed during a total of 27 control periods (six-month periods during which they received placebo) and 24 test periods (six-month periods during which they received immune milk). One patient had sustained a physical injury to one of his ankles and feet. The pain in these joints was not evaluated, which accounts for there being a smaller number of periods of evaluation for these joints. The erythrocyte sedimentation rates for one patient were so extremely abnormal (more than two standard deviations removed from the mean of the values for the other patients) that they were not included. This omission accounts for the smaller number of observations reported for that variable.

The mean values and coefficients of variation (C.V.) are listed in the table for each variable. Differences between the means were calculated by subtracting the mean value obtained during the periods the patients received immune milk from that obtained during the periods they received the placebo. A favorable response to immune milk is indicated by negative values for AM stiffness (question 1) and Monthly change (questions 6a, b, and c) and by positive values for all other variables. An effective response to immune milk was obtained for all data obtained from the questionnaires. Probabilities (P) indicate a high degree of statistical significance in every instance. The small mean differences obtained for erythrocyte sedimentation rate and rheumatoid factor titer were not significant. When erythrocyte sedimentation rates were considered on an individual basis, however, four of the twenty patients studied had statistically significant decreases while receiving immune milk.

Although immune milk had no significant effect on the mean values for rheumatoid factor titer, examination of individual patients revealed some interesting responses. Seven of the twenty patients studied had negative rheumatoid factor titers on at least one occasion during the period they were receiving immune milk. Four of them became negative during the period that they received immune milk and their titers failed to become positive during the following six-month period when they received the control (placebo) milk as shown in FIG. 2. Continuation of the study past this reporting period reveals that 13 of 25 patients lost the rheumatoid factor from their blood.

Discussion

The scientist in charge of this study personally interviewed each patient at monthly intervals, and recorded their answers to the questions. Every effort was made not to influence the patient's answers. The patients were initially informed and were frequently reminded that, during certain periods of the study, they would receive a placebo. It was anticipated that this knowledge would serve as an inducement for the patients to answer the questions objectively and without bias. At no time were the patients informed whether they were receiving immune milk or the placebo.

The question regarding medication taken "yesterday" (question #3) and the question regarding gold shots, Plaquenil and cortisone shots (question #4) are objective and are of primary importance in considering answers given to the other questions. These questions are important for two reasons:

(1) if the immune milk is effective in relieving symptoms of the disease, the patient would be expected to take fewer medicines that were allowed ad libitum. On an average, patients reported that they took four less aspirins or their equivalent per day during the periods that they received immune milk. They also reported that they received fewer gold shots, Plaquenil and cortisone shots during these periods; and (2) if patients took smaller quantities of analgesics and other medicines useful in the treatment of rheumatoid arthritis, one would expect them to report increased discomfort unless the immune milk was influencing the disease favorably.

As noted in Table 2, significantly less joint involvement was reported during periods that the patients received immune milk even though they were taking less medicines for their arthritis.

Patients started on the study at monthly intervals over a one-year period, and the type of milk product (immune milk or placebo) that they initially received was randomized. The observation that positive responses or improvement were obtained for all parameters of the questionnaire, and that these mean responses were statistically significant strongly indicate that immune milk had a beneficial effect on the patients. This conclusion is reinforced by the observation that 20% of the patients experienced a statistically significant ($p<0.05$) decrease in erythrocyte sedimentation rate while receiving immune milk.

Results of the rheumatoid factor titers are difficult to evaluate. This is due at least in part to the fact that the origin and role of rheumatoid factors in the etiology and prognosis of rheumatoid arthritis is not understood. Rose et al (1948) showed that sheep red blood cells that were sensitized with rabbit antibody underwent agglutination in the presence of blood serum from patients with rheumatoid arthritis. The test depends on the specific reaction between normal immunoglobulin (either rabbit or human $I_gG$) with rheumatoid factors. The specificities exhibited by rheumatoid factor are like those that would be expected of antibody against $I_gG$ (Epstein, et al, 1956) Proc. Soc. Exp. Biol. Med. 91:235. The presence of rheumatoid factors has been correlated with disease severity in rheumatoid arthritis and can be identified in proteins precipitated in the tissues of patients with rheumatoid arthritis. Although a small percentage of patients with rheumatoid arthritis do not have positive rheumatoid factor titers, it is generally agreed by most rheumatologists that positive agglutination reactions do not revert to negative even when the disease is in remission. DeForest, et al (1958) Arth. & Rheum. 1:387, however, described a small number of patients who had positive rheumatoid factor titers that reverted to negative following a remission. When recrudescense of the disease occurred, the test again became positive. Aho, et al (1959) Ann. Exp. Fenn. 37:377 noted, however, that most patients whose disease had become inactive remained serologically positive. The fact that negative titers were observed in 60% of our patients and that in half of these, the titers remained negative for six months, proves that immune milk is affecting a primary etiologic factor responsible for rheumatoid arthritis.

The effect of immune milk in alleviating the symptoms of rheumatoid arthritis is particularly relevant when considered on the basis of the recently described relationship between the histocompatibility antigens (HL-A) and the susceptiblity to rheumatic disease (Brewerton, 1976) Arth. & Rheum. 19:656. Histocompatibility antigens are genetically determined antigens that are found on all human cells. The genes controlling their inheritance are called histocompatibility genes. There are now known to be over 40 of these genetically determined antigens. They are responsible for rejection of tissue grafts made between individuals other than identical twins. Superficially the HL-A antigens resemble ABO blood groups in that they are inherited for a lifetime. Their functions is not yet known, except in the highly artificial situation produced by transplantation. It is known, however, that the histocompatibility genes are closely linked with the immune response genes on the sixth chromosome. In this relationship, they may determine the immune response of the individual to a foreign invader, such as a bacteria.

Persons with HLA-B27 appear to be particularly susceptible to a variety of rheumatic diseases. It is postulated that this histocompatibility antigen dictates a type of immune response which in the presence of other predisposing factors leads to rheumatoid arthritis. After an intestinal infection with *Yersinia enterocolitica*, some patients develop an acute peripheral arthritis (Ahvonen, et al, 1969) Acta. Rheum. Scand. 15:232. Similarly, after salmonella infection, about 2% of patients develop acute peripheral arthritis (Warren, Am. Rheum. Dis. 29:484 1970). HLA-B27 was found in 43 of 49 patients with yersinia arthritis and in 15 of 16 with salmonella arthritis (Aho, 1974) Ann. Exp. Fenn. 37:377. It is an attractive possibility that infective agents may thrive in the intestinal tract without giving rise to local symptoms. In patients with HLA-B27, a host response is established that results in arthritis. *Thus, it is not necessary for the infective agent to gain entry into the joints. Immune milk is beneficial to patients with rheumatoid arthritis because it contains antibodies that effectively inactivate or neutralize offending bacteria and/or their metabolic products.*

We claim:

1. A method for the treatment of rheumatoid arthritis caused by a mixed spectrum of infectious bacteria which reside in the gastrointestinal tract, including:

| ORGANISMS |
| --- |
| *Staphylococcus aureus* |
| *Staphylococcus epidermidis* |
| *Streptococcus pyogenes*, A. Type 1 |
| *Streptococcus pyogenes*, A. Type 3 |
| *Streptococcus pyogenes*, A. Type 5 |
| *Streptococcus pyogenes*, A. Type 8 |
| *Streptococcus pyogenes*, A. Type 12 |
| *Streptococcus pyogenes*, A. Type 14 |
| *Streptococcus pyogenes*, A. Type 18 |
| *Streptococcus pyogenes*, A. Type 22 |
| *Aerobacter aerogenes* |
| *Escherichia coli* |
| *Salmonella enteritidis* |
| *Pseudomonas aeruginosa* |
| *Klebsiella pneumoniae* |
| *Salmonella typhimurium* |
| *Haemophilus influenzae* |
| *Streptococcus viridans* |
| *Proteus vulgaris* |
| *Shigella dysenteriae* |
| Streptococcus, Group B |
| *Diplococcus pneumoniae* |
| *Streptococcus mutans* |
| Corynebacterium, Acne, Types 1 & 2 | which comprises the oral administration of a quantity of non-fat milk solids equivalent to one quart of immunized cow's milk IgG, post-prandially two times daily, wherein the cow's milk IgG includes antibodies produced by the following microorganisms from American Type Culture Collection bacterial antigens:

| ORGANISMS | *ATCC NO. |
| --- | --- |
| *Staphylococcus aureus* | 11631 |
| *Staphylococcus epidermidis* | 155 |
| *Streptococcus pyogenes*, A. Type 1 | 8671 |
| *Streptococcus pyogenes*, A. Type 3 | 10389 |
| *Streptococcus pyogenes*, A. Type 5 | 12347 |
| *Streptococcus pyogenes*, A. Type 8 | 12349 |
| *Streptococcus pyogenes*, A. Type 12 | 11434 |
| *Streptococcus pyogenes*, A. Type 14 | 12972 |
| *Streptococcus pyogenes*, A. Type 18 | 12357 |
| *Streptococcus pyogenes*, A. Type 22 | 10403 |
| *Aerobacter aerogenes* | 884 |
| *Escherichia coli* | 26 |
| *Salmonella enteritidis* | 13076 |
| *Pseudomonas aeruginosa* | 7700 |
| *Klebsiella pneumoniae* | 9590 |
| *Salmonella typhimurium* | 13311 |
| *Haemophilus influenzae* | 9333 |
| *Streptococcus viridans* | 6249 |
| *Proteus vulgaris* | 13315 |
| *Shigella dysenteriae* | 11835 |
| Streptococcus, Group B | |
| *Diplococcus pneumoniae* | |
| *Streptococcus mutans* | |

-continued

| ORGANISMS | *ATCC NO. |
|---|---|
| Corynebacterium, Acne, Types 1 & 2 | |

2. An antibody for the treatment of rheumatoid arthritis caused by a mixed spectrum of infectious bacteria which reside in the gastrointestinal tract, including:

| ORGANISMS |
|---|
| *Staphylococcus aureus* |
| *Staphylococcus epidermidis* |
| *Streptococcus pyogenes*, A. Type 1 |
| *Streptococcus pyogenes*, A. Type 3 |
| *Streptococcus pyogenes*, A. Type 5 |
| *Streptococcus pyogenes*, A. Type 8 |
| *Streptococcus pyogenes*, A. Type 12 |
| *Streptococcus pyogenes*, A. Type 14 |
| *Streptococcus pyogenes*, A. Type 18 |
| *Streptococcus pyogenes*, A. Type 22 |
| *Aerobacter aerogenes* |
| *Escherichia coli* |
| *Salmonella enteritidis* |
| *Pseudomonas aeruginosa* |
| *Klebsiella pneumoniae* |
| *Salmonella typhimurium* |
| *Haemophilus influenzae* |
| *Streptococcus viridans* |
| *Proteus vulgaris* |
| *Shigella dysenteriae* |
| Streptococcus, Group B |
| *Diplococcus pneumoniae* |
| *Streptococcus mutans* |
| Corynebacterium, Acne, Types 1 & 2 | produced by first preparing a vaccine from killed bacteria from the American Type Culture Collection bacterial antigens, including:

| | |
|---|---|
| *Staphylococcus aureus* | 11631 |
| *Staphylococcus epidermidis* | 155 |
| *Streptococcus pyogenes*, A. Type 1 | 8671 |
| *Streptococcus pyogenes*, A. Type 3 | 10389 |
| *Streptococcus pyogenes*, A. Type 5 | 12347 |
| *Streptococcus pyogenes*, A. Type 8 | 12349 |
| *Streptococcus pyogenes*, A. Type 12 | 11434 |
| *Streptococcus pyogenes*, A. Type 14 | 12972 |
| *Streptococcus pyogenes*, A. Type 18 | 12357 |
| *Streptococcus pyogenes*, A. Type 22 | 10403 |
| *Aerobacter aerogenes* | 884 |
| *Escherichia coli* | 26 |
| *Salmonella enteritidis* | 13076 |
| *Pseudomonas aeruginosa* | 7700 |
| *Klebsiella pneumoniae* | 9590 |
| *Salmonella typhimurium* | 13311 |
| *Haemophilus influenzae* | 9333 |
| *Streptococcus viridans* | 6249 |
| *Proteus vulgaris* | 13315 |
| *Shigella dysenteriae* | 11835 |
| Streptococcus, Group B | |
| *Diplococcus pneumoniae* | |
| *Streptococcus mutans* | |
| Corynebacterium, Acne, Types 1 & 2 | | injecting said vaccine intramuscularly in healthy cows once weekly for four consecutive weeks, and twice monthly thereafter, each injection involving $20 \times 10^8$ bacterial cells; collecting the milk from the immunized cows beginning the fourth week; and testing fro titer to insure that the minimum titer against each of the bacteria is 1–500, as determined by the tube agglutination method for testing antibody titer.

3. The preparation of claim 2, wherein the antibody product type IgG is pure immunoglobulin obtained from milk.

4. The method of preparing the antibody of claim 2, which includes preparing a vaccine from killed bacteria from the American Type Culture Collection bacterial antigens including:

| | |
|---|---|
| *Staphylococcus aureus* | 11631 |
| *Staphylococcus epidermidis* | 155 |
| *Streptococcus pyogenes*, A. Type 1 | 8671 |
| *Streptococcus pyogenes*, A. Type 3 | 10389 |
| *Streptococcus pyogenes*, A. Type 5 | 12347 |
| *Streptococcus pyogenes*, A. Type 8 | 12349 |
| *Streptococcus pyogenes*, A. Type 12 | 11434 |
| *Streptococcus pyogenes*, A. Type 14 | 12972 |
| *Streptococcus pyogenes*, A. Type 18 | 12357 |
| *Streptococcus pyogenes*, A. Type 22 | 10403 |
| *Aerobacter aerogenes* | 884 |
| *Escherichia coli* | 26 |
| *Salmonella enteritidis* | 13076 |
| *Pseudomonas aeruginosa* | 7700 |
| *Klebsiella pneumoniae* | 9590 |
| *Salmonella typhimurium* | 13311 |
| *Haemophilus influenzae* | 9333 |
| *Streptococcus viridans* | 6249 |
| *Proteus vulgaris* | 13315 |
| *Shigella dysenteriae* | 11835 |
| Streptococcus, Group B | |
| *Diplococcus pneumoniae* | |
| *Streptococcus mutans* | |
| Corynebacterium, Acne, Types 1 & 2 | | injecting said vaccine intramuscularly in healthy cows and weekly for four consecutive weeks, and twice monthly thereafter, each injections involving $20 \times 10^8$ bacterial cells, collecting the milk from the immunized cows beginning the fourth week; and testing for titer to insure that the minumum titer of antibody against each of the bacteria is 1–500, as determined by the tube agglutination method for testing antibody titer.

* * * * *